United States Patent
Bollyky et al.

(10) Patent No.: US 10,835,607 B2
(45) Date of Patent: Nov. 17, 2020

(54) MONOCLONAL ANTIBODY AND VACCINE TARGETING FILAMENTOUS BACTERIOPHAGE

(71) Applicant: INIMMUNE CORPORATION, Missoula, MT (US)

(72) Inventors: Paul L. Bollyky, Stanford, CA (US); William Parks, Seattle, WA (US); Patrick Secor, Seattle, WA (US)

(73) Assignee: INIMMUNE CORPORATION, Missoula, MT (US)

( * ) Notice: Subject to any disclaimer, the term of this patent is extended or adjusted under 35 U.S.C. 154(b) by 0 days.

(21) Appl. No.: 16/262,548

(22) Filed: Jan. 30, 2019

(65) Prior Publication Data

US 2020/0038510 A1 Feb. 6, 2020

Related U.S. Application Data

(63) Continuation of application No. 15/219,073, filed on Jul. 25, 2016, now abandoned.

(60) Provisional application No. 62/196,147, filed on Jul. 23, 2015.

(51) Int. Cl.
| | | |
|---|---|---|
| A61K 47/64 | (2017.01) | |
| A61K 39/104 | (2006.01) | |
| A61K 39/00 | (2006.01) | |
| C07K 16/08 | (2006.01) | |
| A61K 45/06 | (2006.01) | |

(52) U.S. Cl.
CPC ............ *A61K 45/06* (2013.01); *A61K 39/104* (2013.01); *A61K 47/646* (2017.08); *C07K 16/08* (2013.01); *A61K 39/00* (2013.01); *C07K 2317/76* (2013.01)

(58) Field of Classification Search
None
See application file for complete search history.

(56) References Cited

U.S. PATENT DOCUMENTS

2003/0113742 A1* 6/2003 Whiteley ........... A61K 38/1709
435/6.18

FOREIGN PATENT DOCUMENTS

| WO | WO 2008/094942 A2 | 8/2008 |
| WO | WO 2009/064854 A2 | 5/2009 |
| WO | WO 2011/111180 A1 | 9/2010 |

OTHER PUBLICATIONS

Asakura et al. Interaction between Particles Suspended in Solutions of Macromolecules. J Polym Sci 33:183-192 (1958).
Boulanger. Purification of bacteriophages and SOS-PAGE analysis of phage structural proteins from ghost particles. Methods Mol Biol 502:227-238 (2009).
Brandt et al. DNA concentration and length in sputum of patients with cystic fibrosis during inhalation with recombinant human DNase. Thorax 50:880-882 (1995).
Castang, S. et al. (2012) "Basis for the Essentiality of H-NS Family Members in Pseudomonas aeruginosa," J Bacteriol. 194(18):5101-5109.
Chang et al. Alginate production by Pseudomonas putida creates a hydrated microenvironment and contributes to biofilm architecture and stress tolerance under water-limiting conditions. J Bacteriol 189:8290-8299 (2007).
Costerton, J.W. et al. (1999) "Bacterial Biofilms: A Common Cause of Persistent Infections," Science 284(5418):1318-1322.
Dogic et al. Elongation and fluctuations of semiflexible polymers in a nematic solvent. Phys Rev Lett 92:125503 (2004).
Dogic et al. Ordered phases of filamentous viruses. Curr Opin Colloid in 11 :47-55 (2006).
Finnan et al. Genome diversity of Pseudomonas aeruginosa isolates from cystic fibrosis patients and the hospital environment. J Clin Microbiol 42:5783-5792 (2004).
Folsom et al. Physiology of Pseudomonas aeruginosa in biofilms as revealed by transcriptome analysis. BMC Microbial 10:294 (2010).
Fothergill et al. Transmissible strains of Pseudomonas aeruginosa in cystic fibrosis lung infections. Eur Respir J 40:227-238 (2012).
Gill et al. Proteoglycans: key regulators of pulmonary inflammation and the innate immune response to lung infection. Anat Rec (Hoboken) 293:968-981 (2010).
Glazer et al. An automatic optical imaging system for birefringent media. Pro R Soc Lond A 452:2751-2765 (1996).
Häußler. Biofilm formation by the small colony variant phenotype of Pseudomonas aeruginosa. Environ Microbial 6:546-551 (2004).β
Hentzer et al. Transcriptome analysis of Pseudomonas aeruginosa biofilm development: anaerobic respiration and iron limitation. Biofilms 2:37-61 (2005).
Hoang et al. A broad-host-range Flp-FRT recombination system for site-specific excision of chromosomally-located DNA sequences: application for isolation of unmarked Pseudomonas aeruginosa mutants. Gene 212:77-86 (1998).
Høby et al. Pseudomonas aeruginosa biofilms in cystic fibrosis. Future Microbial 5:1663-1674 (2010).
Hood et al. A type VI secretion system of Pseudomonas aeruginosa targets a toxin to bacteria. Cell Host Microbe 7:25-37 (2010).
Hunt et al. Macromolecular mechanisms of sputum inhibition of tobramycin activity. Antimicrob Agents Chemother 39:34-39 (1995).
Jarvis. Benchmarking for prevention: the Centers for Disease Control and Prevention's National Nosocomial Infections Surveillance (NNIS) system experience. Infection 31 Suppl 2:44-48 (2003).

(Continued)

*Primary Examiner* — Sarvamangala Devi
(74) *Attorney, Agent, or Firm* — Michael Best & Friedrich LLP

(57) ABSTRACT

Described here is a method for reducing or preventing *Pseudomonas aeruginosa* biofilm formation in a human subject in need thereof, comprising administering to the human subject a first composition comprising (a) an antigen-binding polypeptide that binds Pf-family bacteriophage, or (b) a vaccine against Pf-family bacteriophage. Also described is an antigen-binding polypeptide that binds specifically to a CoaB protein of Pf-family bacteriophage or fragment thereof.

2 Claims, 13 Drawing Sheets

Specification includes a Sequence Listing.

(56) References Cited

OTHER PUBLICATIONS

Jones et al. Identification of airborne dissemination of epidemic multiresistant strains of Pseudomonas aeruginosa at a CF centre during a cross infection outbreak. Thorax 58:525-527 (2003).
Kirov et al. Biofilm differentiation and dispersal in mucoid Pseudomonas aeruginosa isolates from patients with cystic fibrosis. Microbiology 153:3264-327 4 (2007).
Manos et al. Transcriptome analyses and biofilm-forming characteristics of a clonal Pseudomonas aeruginosa from the cystic fibrosis lung. J Med Microbiol 57:1454-1465 (2008).
Mathee et al. Dynamics of Pseudomonas aeruginosa genome evolution. PNAS USA 105:3100-3105 (2008).
Matsui et al. A physical linkage between cystic fibrosis airway surface dehydration and Pseudomonas aeruginosa biofilms. PNAS USA 103:18131-18136 (2006).
Mcelroy et al. Strain-specific parallel evolution drives short-term diversification during Pseudomonas aeruginosa biofilm formation. PNAS USA 111:E1419-1427 (2014).
Mooij et al. Characterization of the integrated filamentous phage Pf5 and its involvement in small-colony formation. Microbiology 153:1790-1798 (2007).
Onsager. The effects of shape on the interaction of colloidal particles. Ann NY Acad Sci 51:627-659 (1949).
Ophir et al. A role for exopolysaccharides in the protection of microorganisms from desiccation. Appl Environ Microbiol 60:740-745 (1994).
Panagea et al. Environmental contamination with an epidemic strain of Pseudomonas aeruginosa in a Liverpool cystic fibrosis centre, and study of its survival on dry surfaces. J Hosp Infect 59:102-107 (2005).
Parsley et al. Identification of diverse antimicrobial resistance determinants carried on bacterial, plasmid, or viral metagenomes from an activated sludge microbial assemblage. Appl Environ Microbial 76:3753-3757 (2010).
Petrova et al. The novel Pseudomonas aeruginosa two-component regulator BfmR controls bacteriophage-mediated lysis and DNA release during biofilm development through PhdA. Mol Microbial 81:767-783 (2011 ).
Platt et al. Proteomic, microarray, and signature-tagged mutagenesis analyses of anaerobic Pseudomonas aeruginosa at pH 6.5, likely representing chronic, late-stage cystic fibrosis airway conditions. J Bacterial 190:2739-2758 (2008).
Poon. The physics of a model colloid-polymer mixture. J Phys-Condens Mat 14:R859-R880 (2002).
Rakonjac et al. Filamentous Bacteriophage: Biology, Phage Display and Nanotechnology Applications. Curr Issues Mol Biol 13:51-76 (2011).
Rice, S.A. et al. (2009) "The biofilm life cycle and virulence of Pseudomonas aeruginosa are dependent on a filamentous prophage," The ISME Journal 3:271-282.
Schmidt et al. Viscoelastic properties of semiflexible filamentous bacteriophage fd. Phys Rev E Stat Phys Plasmas Fluids Relat Interdiscip Topics 62:5509-5517 (2000).
Schulz et al. Cystic fibrosis transmembrane conductance regulator can export hyaluronan. Pathobiology 77:200-209 (2010).
Secor, P.R. et al. (2015) "Filamentous Bacteriophage Promote Biofilm Assembly and Function," Cell Host & Microbe 18:549-559.
Shak et al. Recombinant human DNase I reduces the viscosity of cystic fibrosis sputum. PNAS USA 87:9188-9192 (1990).
Stewart, P.S. (2002) "Mechanisms of antibiotic resistance in bacterial biofilms," Int J Med Microbial. 292(2):107-113.
Tseng et al. The extracellular matrix protects Pseudomonas aeruginosa biofilms by limiting the penetration of tobramycin. Environ Microbial 15:2865-2878 (2013).
Vasconcellos et al. Reduction in viscosity of cystic fibrosis sputum in vitro by gelsolin. Science 263:969-971 (1994).
Waldor et al. Lysogenic conversion by a filamentous phage encoding cholera toxin. Science 272:1910-1914 (1996).
Walters et al. Contributions of antibiotic penetration, oxygen limitation, and low metabolic activity to tolerance of Pseudomonas aeruginosa biofilms to ciprofloxacin and tobramycin. Antimicrob Agents Chemother 47:317-323 (2003).
Webb et al. Cell death in Pseudomonas aeruginosa biofilm development. J Bacterial 185:4585-4592 (2003).
Webb, J.S. et al. (2004) "Bacteriophage and Phenotypic Variation in Pseudomonas aeruginosa Biofilm Development," J. Bacterial. 186(23):8066-8073.
Whitchurch et al. Extracellular DNA required for bacterial biofilm formation. Science 295:1487 (2002).
Whiteley et al. Gene expression in Pseudomonas aeruginosa biofilms. Nature 413:860-864 (2001).
Winstanley et al. Newly introduced genomic prophage islands are critical determinants of in vivo competitiveness in the Liverpool Epidemic Strain of Pseudomonas aeruginosa. Genome Res 19:12-23 (2009).
Wnorowska et al. Bactericidal activity of cathelicidin LL-37 and select cationic lipids against the hypervirulent P. aeruginosa strain LESB58. Antimicrob Agents Chemother 59(7):3808-3815 (2015).
Yeung et al. Swarming of Pseudomonas aeruginosa is controlled by a broad spectrum of transcriptional regulators, including MetR. J Bacterial 191 :5592-5602 (2009).
Yokoyama, WM. Et al. (2013) "Production of Monoclonal Antibodies," Current Protocols in Immunology 102: II :2.5:2.5.1-2.5.29.
Zhao et al. Psl trails guide exploration and microcolony formation in Pseudomonas aeruginosa biofilms. Nature 497:388-391 (2013).

* cited by examiner

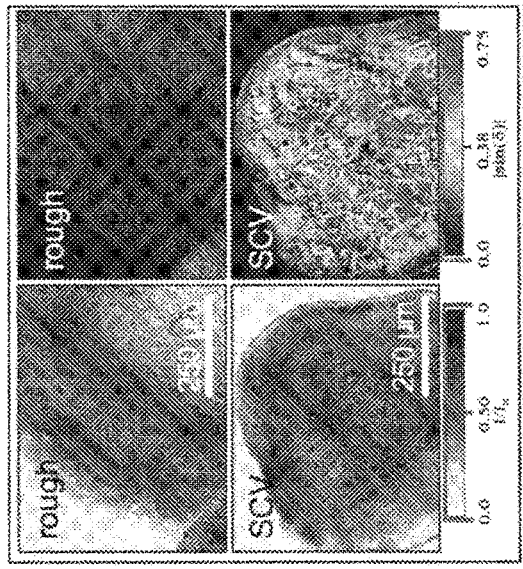
FIG. 1A
FIG. 1B
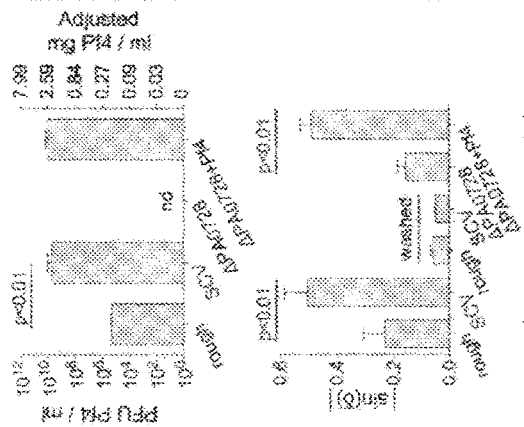
FIG. 1C
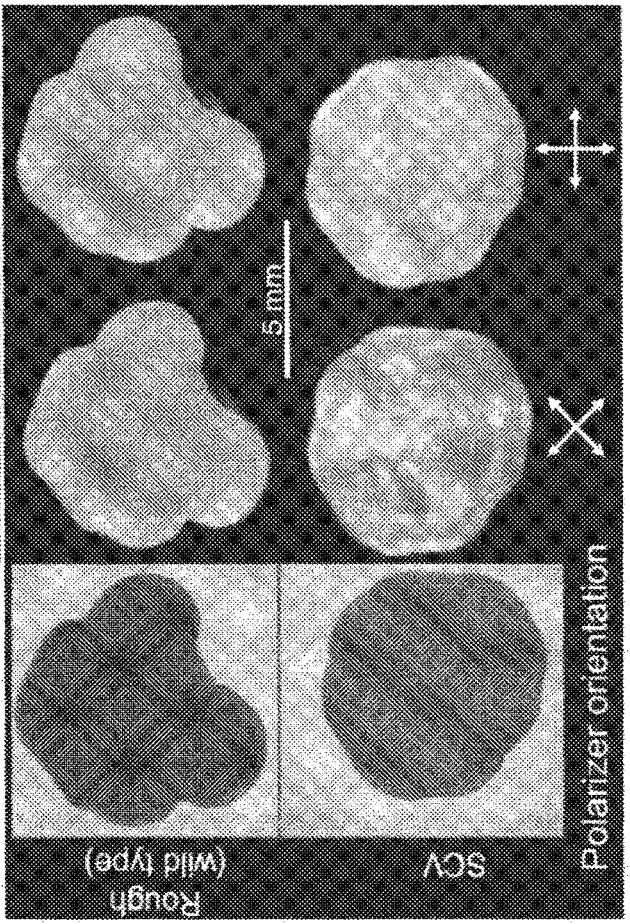
FIG. 1D

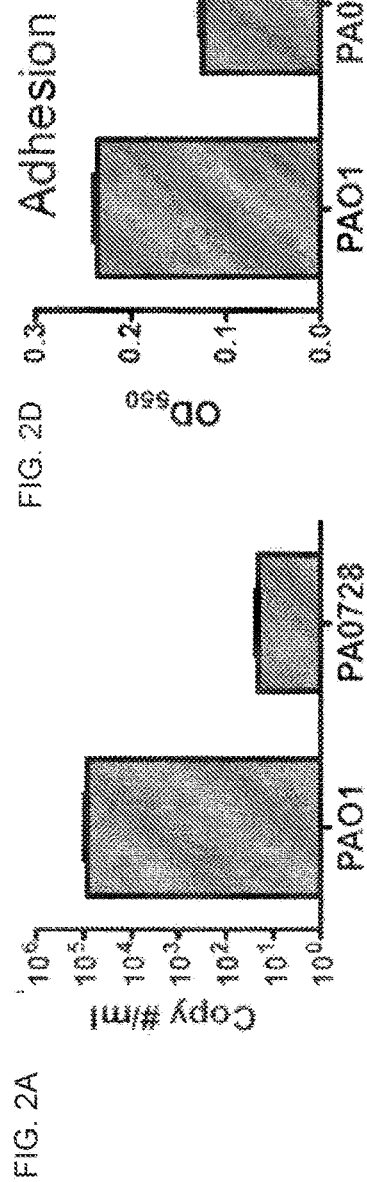
FIG. 2A
FIG. 2B
FIG. 2C
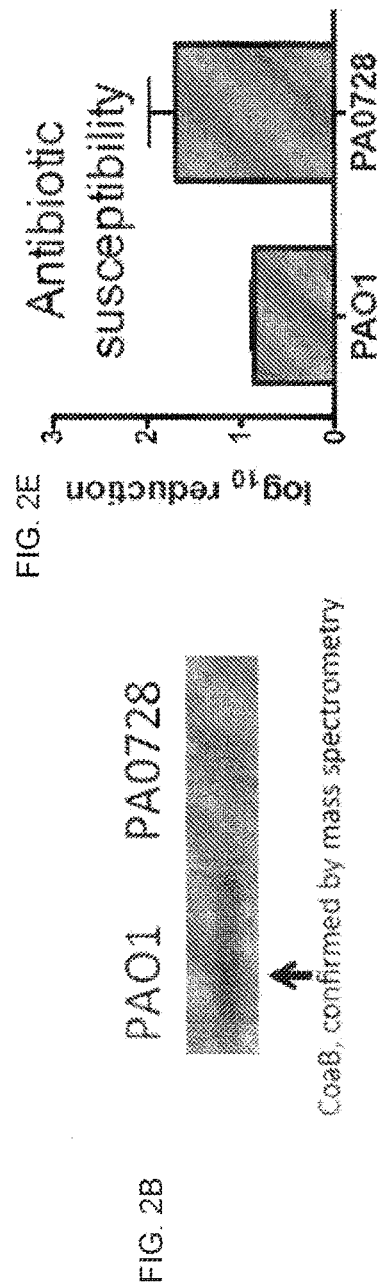
FIG. 2D
FIG. 2E
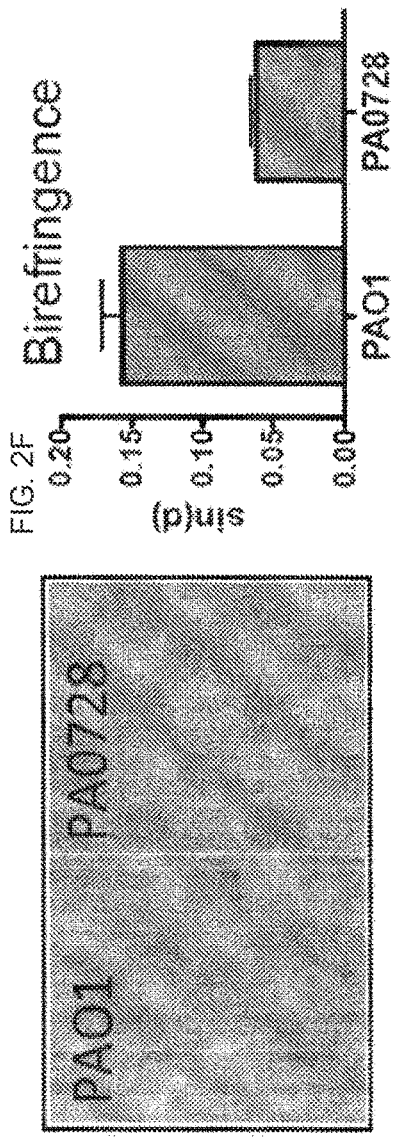
FIG. 2F

SEQUENCE LISTING

<160> NUMBER OF SEQ ID NOS: 31

<210> SEQ ID NO 1
<211> LENGTH: 19
<212> TYPE: PRT
<213> ORGANISM: Pseudomonas phage

<400> SEQUENCE: 1

Gly Val Ile Asp Thr Ser Ala Val Glu Ser Ala Ile Thr Asp Gly Gln
1               5                   10                  15

Gly Asp Met

<210> SEQ ID NO 2
<211> LENGTH: 116
<212> TYPE: PRT
<213> ORGANISM: Mus sp.

<400> SEQUENCE: 2

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Leu
                85                  90                  95

Arg Gly Gln Asp Tyr Gly Ala Ala Tyr Trp Gly Gln Gly Thr Leu Val
            100                 105                 110

Thr Val Ser Ala
        115

<210> SEQ ID NO 3
<211> LENGTH: 348
<212> TYPE: DNA
<213> ORGANISM: Mus sp.

<400> SEQUENCE: 3
gaagtgaagc tggtggagtc tgggggagac ttagtgaagc tggagggtc cctgaaactc      60 tcctgtgcag cctctggatt cactttcagt agctatgtca tgtcttgggt tcgccagact     120
ccagaaaaga ggctggagtg ggtcgcatcc attagtagtg gtggtagcac ctactatcca     180
gacagtgtga aggccgatt caccatctcc agagataatg ccaggaacat cctgtacctg      240
caaatgagta gtctgaggtc tgaggacacg gccatgtatt actgtttaag aggccaggac     300
tacggcgccg cttactgggg ccaagggact ctggtcactg tctctgca                  348

<210> SEQ ID NO 4
<211> LENGTH: 112
<212> TYPE: PRT
<213> ORGANISM: Mus sp.

```
<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 5
<211> LENGTH: 336
<212> TYPE: DNA
<213> ORGANISM: Mus sp.

<400> SEQUENCE: 5
gatgttgtga tgacccagac tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acatttccct     300
cagacgttcg gtggaggcac caagctggaa atcaaa                               336

<210> SEQ ID NO 6
<211> LENGTH: 8
<212> TYPE: PRT
<213> ORGANISM: Mus sp.

<400> SEQUENCE: 6

Gly Phe Thr Phe Ser Ser Tyr Val
1               5

<210> SEQ ID NO 7
<211> LENGTH: 7
<212> TYPE: PRT
<213> ORGANISM: Mus sp.

<400> SEQUENCE: 7

Ile Ser Ser Gly Gly Ser Thr
1               5

<210> SEQ ID NO 8
<211> LENGTH: 10
<212> TYPE: PRT
<213> ORGANISM: Mus sp.

<400> SEQUENCE: 8

Leu Arg Gly Gln Asp Tyr Gly Ala Ala Tyr
1               5                   10
```

```
<210> SEQ ID NO 9
<211> LENGTH: 11
<212> TYPE: PRT
<213> ORGANISM: Mus sp.

<400> SEQUENCE: 9

Gln Ser Leu Leu Asp Ser Asp Gly Lys Thr Tyr
1               5                   10

<210> SEQ ID NO 10
<211> LENGTH: 3
<212> TYPE: PRT
<213> ORGANISM: Mus sp.

<400> SEQUENCE: 10

Leu Val Ser
1

<210> SEQ ID NO 11
<211> LENGTH: 9
<212> TYPE: PRT
<213> ORGANISM: Mus sp.

<400> SEQUENCE: 11

Trp Gln Gly Thr His Phe Pro Gln Thr
1               5

<210> SEQ ID NO 12
<211> LENGTH: 123
<212> TYPE: PRT
<213> ORGANISM: Mus sp.

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
                20                  25                  30

Trp Met His Trp Val Lys Gln Arg Pro Gly Gln Gly Leu Glu Trp Ile
            35                  40                  45

Gly Ala Ile Tyr Pro Gly Asn Ser Asp Thr Ser Tyr Asn Gln Lys Phe
        50                  55                  60

Lys Gly Lys Ala Lys Leu Thr Ala Val Thr Ser Ala Ser Thr Ala Tyr
65                  70                  75                  80

Met Glu Leu Ser Cys Leu Thr Asn Glu Asp Ser Ala Val Phe Tyr Cys
                85                  90                  95

Thr Arg Ser Gln Phe Tyr Ser Gly Ser Ser Glu Asp Ala Met Asp Tyr
            100                 105                 110

Trp Gly Gln Gly Thr Ser Val Thr Val Ser Ser
        115                 120

<210> SEQ ID NO 13
<211> LENGTH: 369
<212> TYPE: DNA
<213> ORGANISM: Mus sp.

<400> SEQUENCE: 13
gaggttcagc tccagcagtc tgggactgtg ctggcaaggc ctggggcttc cgtgaagatg      60
tcctgcaagg cttctggcta cagctttacc agctactgga tgcactgggt aaaacagagg     120
cctggacagg gtctagaatg gattggtgct atttatcctg gaaatagtga ctactagttac    180 aaccagaagt tcaagggcaa ggccaaactg actgcagtca catccgccag cactgcctac    240
```

```
atggagctca gctgcctgac aaatgaggac tctgcggtct ttactgtac aagatcccaa    300 ttttactccg gtagtagcga ggatgctatg gactactggg gtcaaggaac ctcagtcacc    360
gtctcctca                                                            369
```

<210> SEQ ID NO 14
<211> LENGTH: 112
<212> TYPE: PRT
<213> ORGANISM: Mus sp.

<400> SEQUENCE: 14

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 15
<211> LENGTH: 336
<212> TYPE: DNA
<213> ORGANISM: Mus sp.

<400> SEQUENCE: 15

```
gatgttttga tgacccaaac tccactctcc ctgcctgtca gtcttggaga tcaagcctcc     60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ttcaaggttc acatgttccg    300
tggacgttcg gtggaggcac caagctggaa atcaaa                              336
```

<210> SEQ ID NO 16
<211> LENGTH: 8
<212> TYPE: PRT
<213> ORGANISM: Mus sp.

<400> SEQUENCE: 16

```
Gly Tyr Ser Phe Thr Ser Tyr Trp
1               5
```

<210> SEQ ID NO 17
<211> LENGTH: 8
<212> TYPE: PRT
<213> ORGANISM: Mus sp.

<400> SEQUENCE: 17

```
Ile Tyr Pro Gly Asn Ser Asp Thr
1               5
```

```
<210> SEQ ID NO 18
<211> LENGTH: 16
<212> TYPE: PRT
<213> ORGANISM: Mus sp.

<400> SEQUENCE: 18

Thr Arg Ser Gln Phe Tyr Ser Gly Ser Ser Glu Asp Ala Met Asp Tyr
1               5                   10                  15

<210> SEQ ID NO 19
<211> LENGTH: 11
<212> TYPE: PRT
<213> ORGANISM: Mus sp.

<400> SEQUENCE: 19

Gln Ser Ile Val His Ser Asn Gly Asn Thr Tyr
1               5                   10

<210> SEQ ID NO 20
<211> LENGTH: 3
<212> TYPE: PRT
<213> ORGANISM: Mus sp.

<400> SEQUENCE: 20

Lys Val Ser
1

<210> SEQ ID NO 21
<211> LENGTH: 9
<212> TYPE: PRT
<213> ORGANISM: Mus sp.

<400> SEQUENCE: 21

Phe Gln Gly Ser His Val Pro Trp Thr
1               5

<210> SEQ ID NO 22
<211> LENGTH: 118
<212> TYPE: PRT
<213> ORGANISM: Mus sp.

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Leu Lys Gln Ala Pro Gly Lys Gly Leu Lys Trp Met
        35                  40                  45

Gly Trp Ile Asn Thr Asn Thr Gly Glu Pro Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Lys Asp Tyr Arg Tyr Trp Phe Ala Tyr Trp Gly Gln Gly Thr
            100                 105                 110

Leu Val Thr Val Ser Ala
            115
```

<210> SEQ ID NO 23
<211> LENGTH: 354
<212> TYPE: DNA
<213> ORGANISM: Mus sp.

<400> SEQUENCE: 23

```
cagatccagt tggtgcagtc tggacctgag ctgaagaagc ctggagagac agtcaagatc      60
tcctgcaagg cttctgggta taccttcaca aactatggaa tgaactggct gaagcaggct     120
ccaggaaagg gtttaaagtg gatgggctgg ataaacacca acactggaga gccaacatat     180
gctgaagagt tcaagggacg gtttgccttc tctttggaaa cctctgccag cactgcctat     240
ttgcagatca acaacctcaa aaatgaggac acggctacat atttctgtgc aagaaaggac     300
tataggtact ggtttgctta ctggggccaa gggactctgg tcactgtctc tgca           354
```

<210> SEQ ID NO 24
<211> LENGTH: 112
<212> TYPE: PRT
<213> ORGANISM: Mus sp.

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 25
<211> LENGTH: 336
<212> TYPE: DNA
<213> ORGANISM: Mus sp.

<400> SEQUENCE: 25

```
gatgttttga tgacccaaac tccactctcc ctgcctgtca gtcttggaga tcaagcctcc      60
atctcttgca gatctagtca gagcattgta catagtaatg aaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaa                               336
```

<210> SEQ ID NO 26
<211> LENGTH: 8
<212> TYPE: PRT
<213> ORGANISM: Mus sp.

<400> SEQUENCE: 26

Gly Tyr Thr Phe Thr Asn Tyr Gly
1               5

```
<210> SEQ ID NO 27
<211> LENGTH: 8
<212> TYPE: PRT
<213> ORGANISM: Mus sp.

<400> SEQUENCE: 27

Ile Asn Thr Asn Thr Gly Glu Pro
1               5

<210> SEQ ID NO 28
<211> LENGTH: 11
<212> TYPE: PRT
<213> ORGANISM: Mus sp.

<400> SEQUENCE: 28

Ala Arg Lys Asp Tyr Arg Tyr Trp Phe Ala Tyr
1               5                   10

<210> SEQ ID NO 29
<211> LENGTH: 11
<212> TYPE: PRT
<213> ORGANISM: Mus sp.

<400> SEQUENCE: 29

Gln Ser Ile Val His Ser Asn Gly Asn Thr Tyr
1               5                   10

<210> SEQ ID NO 30
<211> LENGTH: 3
<212> TYPE: PRT
<213> ORGANISM: Mus sp.

<400> SEQUENCE: 30

Lys Val Ser
1

<210> SEQ ID NO 31
<211> LENGTH: 9
<212> TYPE: PRT
<213> ORGANISM: Mus sp.

<400> SEQUENCE: 31

Phe Gln Gly Ser His Val Pro Phe Thr
1               5
```

MONOCLONAL ANTIBODY AND VACCINE TARGETING FILAMENTOUS BACTERIOPHAGE

CROSS-REFERENCE TO RELATED APPLICATIONS

This application is a continuation of U.S. application Ser. No. 15/219,073, filed Jul. 25, 2016, now abandoned, which claims the benefit of U.S. Provisional Patent Application No. 62/196,147 filed Jul. 23, 2015, the content of which is incorporated herein by reference in its entirety.

FEDERAL FUNDING STATEMENT

This invention was made with Government support under contract HL007287 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 30, 2019, is named 53965-701-301-Sequence-Listing.txt and is 12,548 bytes in size.

BACKGROUND

*Pseudomonas aeruginosa* is an opportunistic pathogen in multiple clinical settings, including devastating pulmonary infections in individuals with the genetic disorder cystic fibrosis (CF). The virulence of *P. aeruginosa* is predicated on its ability to form biofilms, which are organized communities of bacteria encased in a polymer-rich matrix. Bacterial biofilms are ubiquitous in nature, and they endow bacteria with the ability to resist antibiotics and evade host immune defense mechanisms. See Costerton et al., *Science* 284:1318 (1999); Stewart et al., *Int. J. Med. Microbiol.* 292:107 (2002).

Thus, a need exists to develop therapeutic agents that can inhibit the formation of *P. aeruginosa* biofilms thereby making *P. aeruginosa* infections more susceptible to antibiotic treatment.

SUMMARY

Many embodiments described herein relate to a method for reducing or preventing *P. aeruginosa* biofilm formation in a human subject in need thereof, comprising administering to the human subject a first composition comprising (a) an antigen-binding polypeptide that binds Pf-family bacteriophage, or (b) a vaccine against Pf-family bacteriophage.

In one embodiment, the first composition comprises an antigen-binding polypeptide. In one embodiment, the antigen-binding polypeptide binds specifically to a CoaB protein of Pf-family bacteriophage or fragment thereof. In one embodiment, the antigen-binding polypeptide is IgG or IgM.

In one embodiment, the first composition further comprises an antibiotic, or the method further comprises administering a second composition comprising an antibiotic to the human subject.

In one embodiment, the human subject is infected with a *P. aeruginosa* strain resistant to one or more antibiotics.

In one embodiment, the first composition comprises a vaccine against Pf-family bacteriophage. In one embodiment, the vaccine comprises an immunogenic fragment of Pf-family bacteriophage.

In one embodiment, the CoaB protein or fragment thereof comprises the amino acid sequence of GVIDTSAVESAITDGQGDM (SEQ ID NO: 1).

In one embodiment, the human subject is suffering from cystic fibrosis, burns, chronic would, chronic rhinosinusitis, ventilator-associated pneumonia, catheter-associated urinary tract infections, septic shock, and/or gastrointestinal infections.

Further embodiments described herein relate to an antigen-binding polypeptide that binds specifically to a CoaB protein of Pf-family bacteriophage or fragment thereof.

In one embodiment, the antigen-binding polypeptide specifically binds to an antigenic fragment of the CoaB protein comprising the amino acid sequence of GVIDTSAVESAITDGQGDM (SEQ ID NO: 1).

In one embodiment, the antigen-binding polypeptide is a monoclonal antibody, a chimeric antibody, a humanized antibody, a Fab fragment, a Fab' fragment, a F(ab')2 fragment, or an scFv molecule. In one embodiment, the antigen-binding polypeptide is IgG or IgM.

Another embodiment described herein relates to a pharmaceutical composition comprising (a) the antigen-binding polypeptide described herein or a fusion molecule comprising the antigen-binding polypeptide, and (b) a pharmaceutically acceptable carrier.

Another embodiment described herein relates to a polynucleotide encoding the antigen-binding polypeptide described herein.

Another embodiment described herein relates to an expression cassette comprising a promoter operably linked to the polynucleotide described herein.

Another embodiment described herein relates to a vector comprising the expression cassette described herein.

Another embodiment described herein relates to a transformed cell comprising the expression cassette or the vector described herein.

Another embodiment described herein relates to a method for producing an antigen-binding polypeptide, comprising culturing the transformed cell described herein, and isolating the antigen-binding polypeptide expressed by the transformed cell.

In one embodiment, the methods herein relate to the co-delivery of antibiotics with the antigen-binding polypeptide (e.g., monoclonal antibody) described herein.

Additional embodiments described herein relate to a vaccine against Pf-family bacteriophage, comprising (a) an immunogenic fragment of CoaB protein of Pf-family bacteriophage, and (b) a pharmaceutically acceptable excipient.

In one embodiment, the immunogenic fragment of CoaB protein consists of the amino acid sequence of GVIDTSAVESAITDGQGDM (SEQ ID NO:1)

These and other features, together with the organization and manner of operation thereof, will become apparent from the following detailed description when taken in conjunction with the accompanying drawings.

BRIEF DESCRIPTION OF THE DRAWINGS

FIG. 1A-1D. Pf 4 bacteriophage organizes *P. aeruginosa* biofilms into a liquid crystalline structure. FIG. 1A: Pf4 production by colony biofilms formed from the indicated strains enumerated as plaque forming units/milliliter (PFU/ml). Two versions of the standard PA01 *P. aeruginosa* lab strain were used: a "rough" strain that produces only a modest biofilm and a small colony variant (SCV) strain that produces robust biofilms. In addition, strain PA0728, a version of PA01 that does not produce Pf phage, was also used. Adjusted total Pf phage content are also plotted on the right axis. Results are mean±SD of three experiments. FIG. 1B: Representative images of rough and SCV colony biofilms showing transmitted light (displayed as $I/I_O$) and birefringence (jsin(d)j). FIG. 1C: Birefringence (sin(d)) of the indicated colony biofilms was quantified after normalizing for sample thickness. Birefringence, the capacity of a material to split light into two beams with perpendicular polarization, is a signature characteristic of crystals, Thus, assessments of birefringence can be used to determine whether a biofilm is a crystal. Birefringence was again measured after washing of the bacteria to remove the extracellular matrix. Results are mean±SD of four experiments. FIG. 1D: Representative images for SVC and "rough" colony biofilms (placed between glass plates) visualized through crossed polarizing lenses. Birefringence is visualized as bright areas where light passes through both polarizing lenses. The birefringence patterns change when the sample is rotated with respect to the polarizing lenses, revealing extended areas of birefringence. Together, the data in FIG. 1A-1D show that biofilms made by *P. aeruginosa* are liquid crystals and that this crystalline organization is dependent on the presence of Pf phage.

FIG. 2A-2F show that a filamentous bacteriophage, Pf4, contributes to *P. aeruginosa* biofilm function. FIG. 2A-2F show data describing biofilm characteristics for two strains of *P. aeruginosa*-PA01 (a standard laboratory strain) and PA0728 (a version of PA01 from which the promoter responsible for Pf phage production has been deleted, such that Pf phage production is reduced). In FIG. 2A, the Pf phage copy number is shown for *P. aeruginosa* strains PA01 and PA0728, as measured by quantitative PCR. In FIG. 2B the amount of CoaB protein, the coat protein that surrounds phage, is shown to be reduced in PA0728 versus PA01 by Mass Spectrometry. In FIG. 2C, the amount of *P. aeruginosa* colony aggregation is shown to be reduced for PA0728 versus PA01. In FIG. 2D, the adhesion of these bacterial colonies is shown for PA0728 versus PA01, as measured in a flow chamber and crystal violet staining. In FIG. 2E, the susceptibility of PA0728 versus PA01 to 10 µg/ml of the antibiotic gentamycin is shown. In FIG. 2F, the birefringence of PA0728 versus PA01 is shown. It has been recently reported that Pf phage contribute to the organization of *P. aeruginosa* biofilms into a liquid crystal and that this contributes to biofilm adhesion and antibiotic tolerance. Together, the data in FIG. 2A-2F show that the presence of Pf phage contributes to *P. aeruginosa* biofilm function. These data are further elaborated upon in Secor et al., *Cell Host & Microbe.*, 18(5):549-559 (2015).

Figure 9:
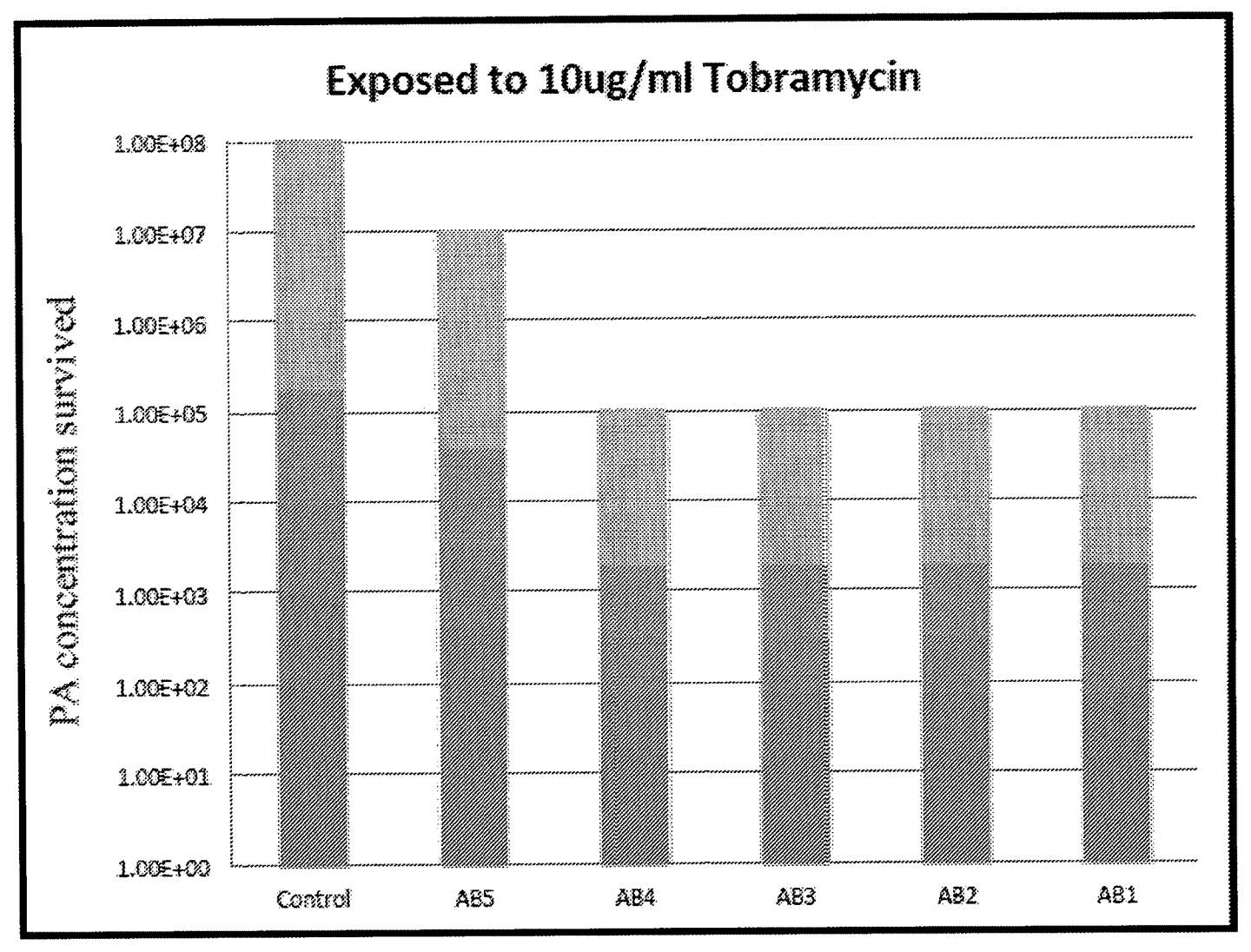

FIG. 9 shows PA concentration survived when exposed to anti-Pf4 antibodies and 10 µg/ml of Tobramycin. This figure provides quantification of the bacterial killing observed in FIG. 8.

Figure 11:
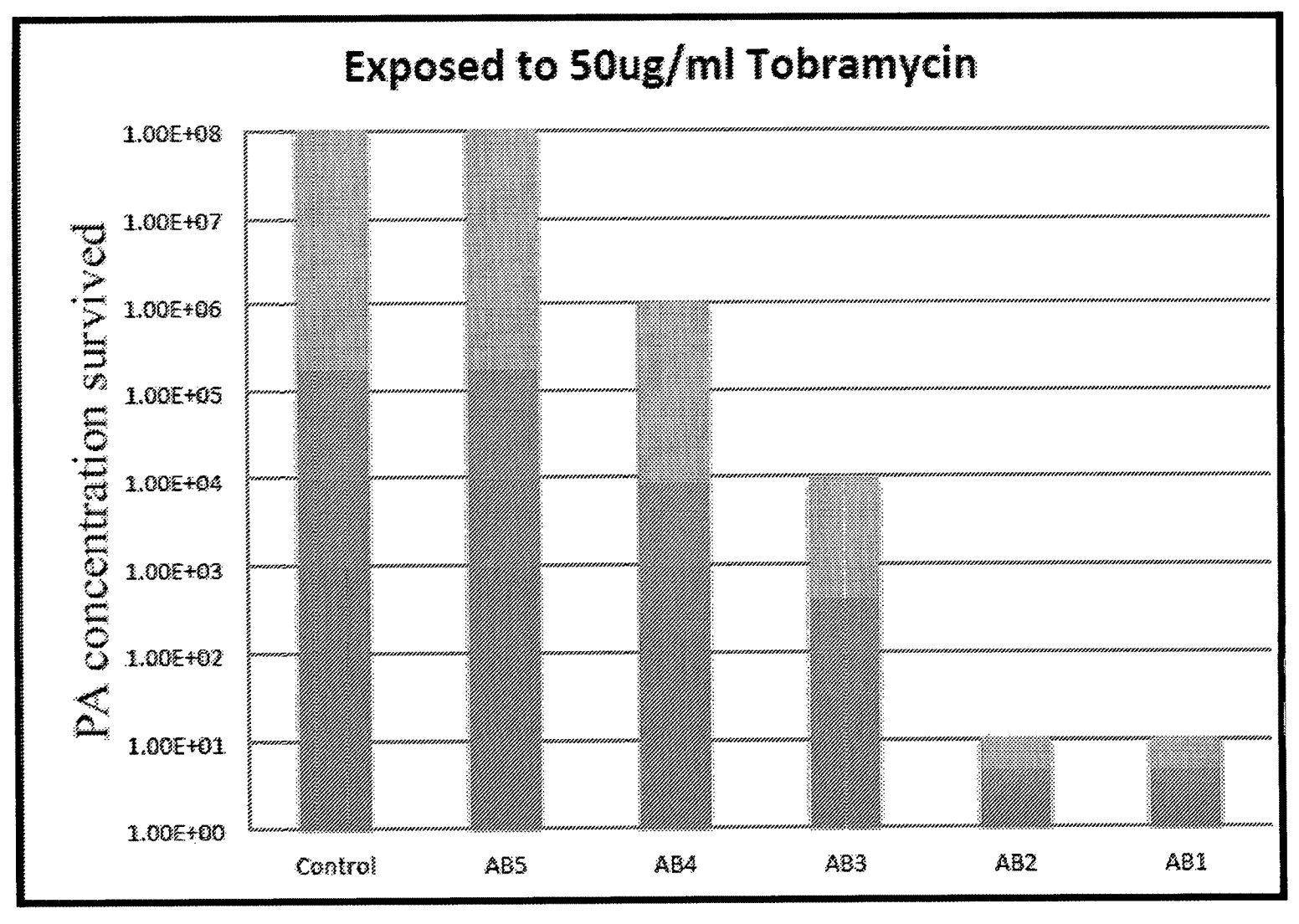

FIG. 11 shows PA concentration survived when exposed to anti-Pf4 antibodies and 50 µg/ml of Tobramycin. This figure provides quantification of the bacterial killing observed in FIG. 10.

DETAILED DESCRIPTION

Introduction

Figure 3:
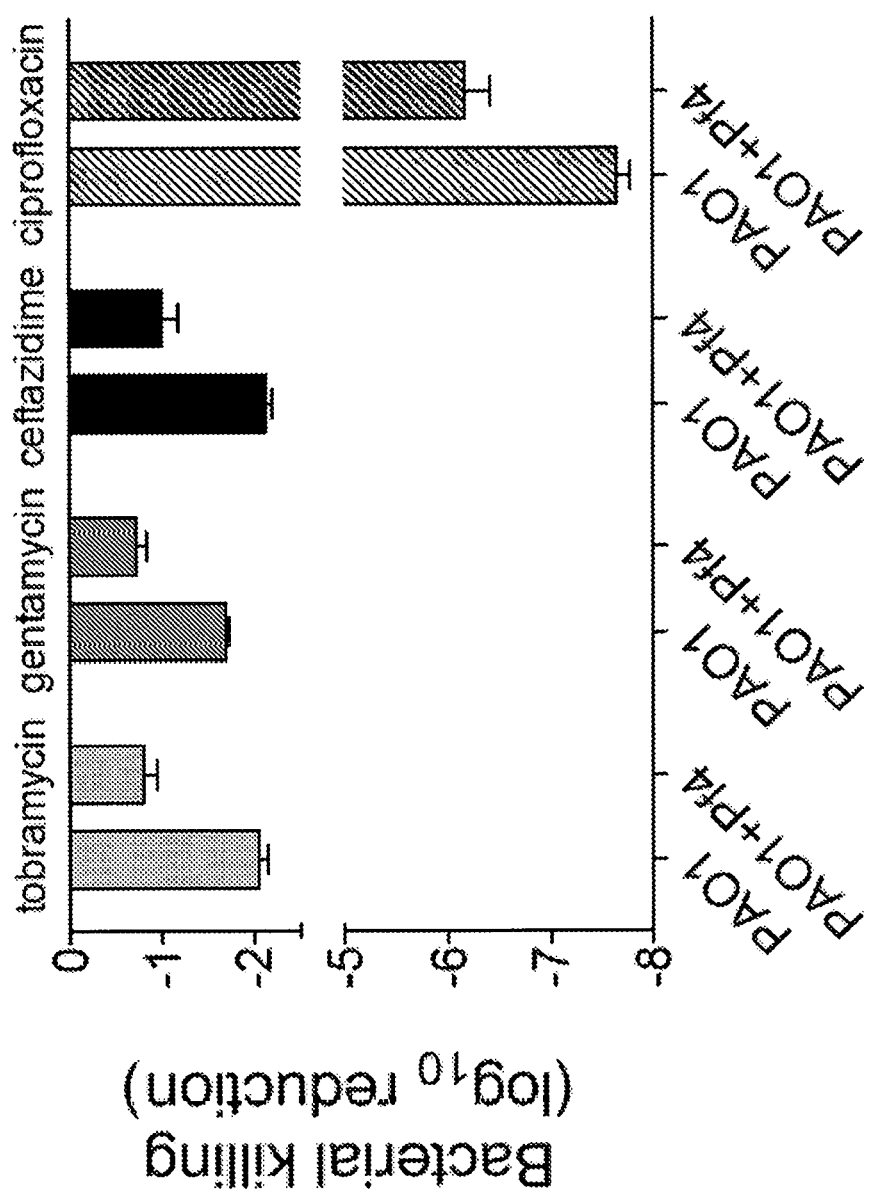
FIG. 3 shows that supplementation of *P. aeruginosa* strain PA01 with Pf4 bacteriophage makes these colonies more tolerant to multiple antibiotics. Killing is represented as the $log_{10}$ reduction of viable cells recovered from cultures treated with different antibiotics, all at 10 mg/ml, compared to untreated controls. Results are mean±SD of three experiments.

Pf-family bacteriophage play a heretofore unappreciated role in microbial biofilm formation. Monoclonal antibodies or immunizations directed against Pf-family bacteriophage provide protection against biofilm-associated infections with *P. aeruginosa* and other microbial pathogens. In particular, *P. aeruginosa* and other Gram-negative microbial pathogens can be resistant to multiple antibiotics, which is an enormous medical problem. Described herein are monoclonal antibodies and immunizations directed against Pf-family bacteriophage which can prevent biofilm formation by these microbes. Therefore, these monoclonal antibodies are an effective class of antibiotic.

In some embodiments, described herein are monoclonal antibodies (both IgG and IgM) directed against conserved regions on the CoaB coat protein of Pf-family bacteriophage. In other embodiments, described herein are synthetic peptides of these same conserved regions on the CoaB coat protein that can be used to immunize animals and human beings against Pf-family bacteriophage. Details of the methods and therapeutic agents of the present invention are provided in the following paragraphs.

Method for Treating/Preventing *P. aeruginosa* Infection

One aspect of the present invention relates to a method for treating or preventing *P. aeruginosa* infection in a human subject, which can be achieved by, for example, reducing or preventing *P. aeruginosa* biofilm formation. The method can comprise, for example, administering to the human subject a composition comprising (a) an antigen-binding polypeptide that binds Pf-family bacteriophage, or (b) a vaccine against Pf-family bacteriophage.

The human subject can be administered with, for example, one or more antigen-binding polypeptides as described herein. The antigen-binding polypeptide can be, for example, an antibody such as IgG or IgM. The antigen-binding polypeptide can bind specifically to, for example, a CoaB protein of Pf-family bacteriophage or fragment thereof. The CoaB protein or fragment thereof can be, for example, the CoaB protein of Pf4 bacteriophage. The CoaB protein or fragment thereof can comprise the amino acid sequence of, for example, GVIDTSAVESAITDGQGDM (SEQ ID NO:1).

The human subject can be administered with, for example, one or more antibiotics. The antibiotics can comprise a known antibiotic against *P. aeruginosa*, which includes but is not limited to, Aminoglycosides (including for example, tobramycin and gentamicin), Cephalosporins (including ceftazidime), and flouroquinolones (including ciprofloxacin). The antibiotics can be administered to the human subject either sequentially or simultaneously with the antigen-binding polypeptides. Without being bound by any theory, it is believed that the antigen-binding polypeptide could reduce or inhibit *P. aeruginosa* biofilm formation, thereby rendering the *P. aeruginosa* more susceptible to antibiotics.

The human subject can be, for example, infected with a *P. aeruginosa* strain resistant to one or more antibiotics. The human subject can be, for example, infected with one or more additional gram negative pathogens.

The human subject can be, for example, suffering from cystic fibrosis. The human subject can be, for example, suffering from burns. The human subject can be, for example, suffering from chronic wounds. The human subject can be, for example, suffering from chronic rhinosinusitis. The human subject can be, for example, suffering from ventilator-associated pneumonia. The human subject can be, for example, suffering from catheter-associated urinary tract infections. The human subject can be, for example, suffering from septic shock. The human subject can be, for example, suffering from gastrointestinal infections.

The human subject can be administered with, for example, a vaccine against Pf-family bacteriophage, such as Pf4 bacteriophage. The vaccine can comprise, for example, an immunogenic fragment of the CoaB protein of Pf-family bacteriophage as described herein.

The human subject being vaccinated can be, for example, an immune-compromised person, such as a person suffering from AIDS. The human subject being vaccinated can be, for example a person over 60 years old, or a person over 65 years old, or a person over 70 years old.

The vaccination can immunize the human subject against, for example, *P. aeruginosa* biofilm formation. The vaccination can immunize the human subject against, for example, *P. aeruginosa* infection.

Antibody Against Pf-Family Bacteriophage

Another aspect of the present invention relates to an antigen-binding polypeptide that binds specifically to CoaB protein of Pf-family bacteriophage or fragment thereof. The CoaB protein or fragment thereof can be, for example, the CoaB protein of Pf4 bacteriophage. The CoaB protein or fragment thereof can comprise the amino acid sequence of, for example, GVIDTSAVESAITDGQGDM (SEQ ID NO:1).

The antigen-binding polypeptide can be, for example, a monoclonal antibody, a chimeric antibody, a humanized antibody, a Fab fragment, a Fab' fragment, a F(ab')2 fragment, or an scFv molecule. The process for making antigen-binding polypeptides are described in, for example, WO/2008/094942, WO/2009/064854, and WO/2010/111180, which are incorporated by reference in their entireties. In one embodiment, the process comprises (a) immunizing a host with an immunogenic polypeptide of a Pf-family bacteriophage, such as an immunogenic fragment of the CoaB protein of Pf4 bacteriophage; and (b) harvesting the resulting antibody against the immunogenic polypeptide.

The antigen-binding polypeptide can be, for example, part of a fusion molecule. The fusion molecule can comprise, for example, a therapeutic or diagnostic agent conjugated to the antigen-binding polypeptide, as described in WO/2008/094942, WO/2009/064854, and WO/2010/111180.

The monoclonal antibodies can also be functionalized to better disrupt biofilms. The functionalized monoclonal antibodies can comprise, for example, enzymes that degrade constituents of the biofilm matrix, such as DNase I or alginate lyase, or charged molecules such as QDOTs or latex beads intended to alter the tertiary structure of the biofilm matrix. Functionalization can also consist of antibiotics, opsonins, reporter molecules, adjuvants, immunogens, or other proteins, carbohydrates or lipids conjugated to the antibodies.

In some embodiments, the antigen-binding polypeptide is an anti-Pf4 monoclonal antibody or fragment thereof. In some embodiments, the monoclonal antibody or fragment thereof specifically binds to the CoaB protein of Pf4 bacteriophage. In some embodiments, the monoclonal antibody or fragment thereof specifically binds to an antigenic fragment of the CoaB protein comprising, consisting essentially of or consisting of the amino acid sequence of GVIDTSAVESAITDGQGDM (SEQ ID NO:1). In some embodiments, the monoclonal antibody or fragment thereof has a humanized heavy chain variable region and a humanized light chain variable region.

In some embodiments, the anti-Pf4 monoclonal antibody or fragment thereof comprises a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8).

In some embodiments, the anti-Pf4 monoclonal antibody or fragment thereof comprises a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18).

In some embodiments, the anti-Pf4 monoclonal antibody or fragment thereof comprises a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28).

In some embodiments, the anti-Pf4 monoclonal antibody or fragment thereof comprises a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the anti-Pf4 monoclonal antibody or fragment thereof comprises a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the anti-Pf4 monoclonal antibody or fragment thereof comprises a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the anti-Pf4 monoclonal antibody or fragment thereof comprises (a) a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8), and (b) a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the anti-Pf4 monoclonal antibody or fragment thereof comprises (a) a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18), and (b) a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the anti-Pf4 monoclonal antibody or fragment thereof comprises (a) a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28), and (b) a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the anti-Pf4 monoclonal antibody or fragment thereof comprises a heavy chain variable region comprising, consisting essentially of or consisting of the amino acid sequence of EVKLVESGGDLVKPGGSLKLSCAASGFTFSSYVMSWVRQTPEKRLEWVA-SISSGGSTYY PDSVKGRFTISRDNARNILYLQMSSLRSEDTAMYYCLRGQDYGAAYWGQGTLVTVSA (SEQ ID NO: 2) or a humanized version thereof.

In some embodiments, the anti-Pf4 monoclonal antibody or fragment thereof comprises a heavy chain variable region comprising, consisting essentially of or consisting of the amino acid sequence of EVQLQQSGTVLARPGASVKMSCKASGYSFTSYWMHWVKQRPGQGLEWIGAI-YPGNSD TSYNQKFKGKAKLTAVTSASTAYMEL-SCLTNEDSAVFYCTRSQFYSGSSEDAMDYWGQ GTSVTVSS (SEQ ID NO: 12) or a humanized version thereof.

In some embodiments, the anti-Pf4 monoclonal antibody or fragment thereof comprises a heavy chain variable region comprising, consisting essentially of or consisting of the amino acid sequence of QIQLVQSGPELKKPGETVKISCKASGYTFTNYGMNWLKQAPGKGLKWMG-WINTNTGEP TYAEEFKGRFAFSLETSASTAYLQINNLKNEDTATYFCARKDYRYWFAYWGQGTLVTV SA (SEQ ID NO: 22) or a humanized version thereof.

In some embodiments, the anti-Pf4 monoclonal antibody or fragment thereof comprises a light chain variable region comprising, consisting essentially of or consisting of the amino acid sequence of DVVMTQTPLTLSVTIGQPASIS-CKSSQSLLDSDGKTYLNWLLQRPGQSPKRLIYL-VSKLD SGVPDRFTGSGSGTDFTLKISRVEAEDL-GVYYCWQGTHFPQTFGGGTKLEIK (SEQ ID NO: 4) or a humanized version thereof.

In some embodiments, the anti-Pf4 monoclonal antibody or fragment thereof comprises a light chain variable region comprising, consisting essentially of or consisting of the amino acid sequence of DVLMTQTPLSLPVSLGDQASIS-CRSSQSIVHSNGNTYLEWYLQKPGQSPKLLIYKVS-NRF SGVPDRFSGSGSGTDFTLKISRVEAEDLGVY-FCFQGSHVPWTFGGGTKLEIK (SEQ ID NO: 14) or a humanized version thereof.

In some embodiments, the anti-Pf4 monoclonal antibody or fragment thereof comprises a light chain variable region comprising, consisting essentially of or consisting of the amino acid sequence of DVLMTQTPLSLPVSLGDQASIS-CRSSQSIVHSNGNTYLEWYLQKPGQSPKLLIYKVS-NRF SGVPDRFSGSGSGTDFTLKISRVEAEDLGVYY-CFQGSHVPFTFGSGTKLEIK (SEQ ID NO: 24) or a humanized version thereof.

Another aspect of the present invention relates to a pharmaceutical composition comprising (a) the antigen-binding polypeptide described herein or a fusion molecule comprising the antigen-binding polypeptide, and (b) a pharmaceutically acceptable carrier. In one embodiment, the active ingredient of the pharmaceutical composition consists essentially of the antigen-binding polypeptide or fusion molecule. In another embodiment, the active ingredient of the pharmaceutical composition consists of the antigen-binding polypeptide or fusion molecule.

Another aspect of the present invention relates to a polynucleotide encoding the antigen-binding polypeptide described herein. The polynucleotide encoding the antigen-binding polypeptide can be comprised in, for example, an expression cassette, with optionally a promoter operably linked to the polynucleotide. The expression cassette can be comprised in, for example, a plasmid or transformation vector. The plasmid or transformation vector can be used to obtain a transformed cell capable of producing the antigen-binding polypeptide encoded therein.

In some embodiments, the polynucleotide encodes a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8).

In some embodiments, the polynucleotide encodes a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQ-FYSGSSEDAMDY (SEQ ID NO: 18).

In some embodiments, the polynucleotide encodes a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28).

In some embodiments, the polynucleotide encodes a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the polynucleotide encodes a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the polynucleotide encodes a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the polynucleotide encodes (a) a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8), and (b) a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the polynucleotide encodes (a) a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQ-FYSGSSEDAMDY (SEQ ID NO: 18), and (b) a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the polynucleotide encodes (a) a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28), and (b) a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the polynucleotide encodes a heavy chain variable region comprising, consisting essentially of or consisting of the amino acid sequence of EVKLVESGGDLVKPGGSLKLSCAASGFTFSSYVM-SWVRQTPEKRLEWVASISSGGSTYY PDSVKGR-FTISRDNARNILYLQMSSLRSEDTAMYYCLRGQDY-GAAYWGQGTLVTVSA (SEQ ID NO: 2) or a humanized version thereof.

In some embodiments, the polynucleotide encodes a heavy chain variable region comprising, consisting essentially of or consisting of the amino acid sequence of EVQLQQSGTVLARPGASVKMSCKASGYSFTSYWM-HWVKQRPGQGLEWIGAIYPGNSD TSYNQKFKG-KAKLTAVTSASTAYMELSCLTNEDSAVFYCTRSQ-FYSGSSEDAMDYWGQ GTSVTVSS (SEQ ID NO: 12) or a humanized version thereof.

In some embodiments, the polynucleotide encodes a heavy chain variable region comprising, consisting essentially of or consisting of the amino acid sequence of QIQLVQSGPELKKPGETVKISCKASGYTFTNYGMN-WLKQAPGKGLKWMGWINTNTGEP TYAEEFKGR-FAFSLETSASTAYLQINNLKNEDTATYFCARKDYRY-WFAYWGQGTLVTV SA (SEQ ID NO: 22) or a humanized version thereof.

In some embodiments, the polynucleotide encodes a light chain variable region comprising, consisting essentially of or consisting of the amino acid sequence of DVVMTQT-PLTLSVTIGQPASISCKSSQSLLDSDGKTYLNWLLQR-PGQSPKRLIYLVSKLD SGVPDRFTGSGSGTDFTLKIS-RVEAEDLGVYYCWQGTHFPQTFGGGTKLEIK (SEQ ID NO: 4) or a humanized version thereof.

In some embodiments, the polynucleotide encodes a light chain variable region comprising, consisting essentially of or consisting of the amino acid sequence of DVLMTQT-PLSLPVSLGDQASISCRSSQSIVHSNGNTYLEWYLQK-PGQSPKLLIYKVSNRF SGVPDRFSGSGSGTDFTLKIS-RVEAEDLGVYFCFQGSHVPWTFGGGTKLEIK (SEQ ID NO: 14) or a humanized version thereof.

In some embodiments, the polynucleotide encodes a light chain variable region comprising, consisting essentially of or consisting of the amino acid sequence of DVLMTQT-PLSLPVSLGDQASISCRSSQSIVHSNGNTYLEWYLQK-PGQSPKLLIYKVSNRF SGVPDRFSGSGSGTDFTLKIS-RVEAEDLGVYYCFQGSHVPFTFGSGTKLEIK (SEQ ID NO: 24) or a humanized version thereof Vaccine Against Pf-Family Bacteriophage A further aspect of the present invention relates to a vaccine against Pf-family bacteriophage, comprising an immunogenic fragment of the CoaB protein of Pf-family bacteriophage. The CoaB protein or fragment thereof can be, for example, the CoaB protein of Pf4 bacteriophage. The CoaB protein or fragment thereof can comprise the amino acid sequence of, for example, GVIDTSAVESAIT-DGQGDM (SEQ ID NO:1).

In some embodiments, the vaccine is used to vaccinate patients newly diagnosed with cystic fibrosis before they become colonized with *P. aeruginosa* or to elderly people before they become prone to catheter infections and hospital-acquired infections. In some embodiments, the vaccine is used to vaccinate nursing home populations, or patients undergoing dialysis, mechanical ventilation or recurrent UTIs, or burn victims.

These and other features, together with the organization and manner of operation thereof, will become apparent from the following detailed description when taken in conjunction with the accompanying drawings.

WORKING EXAMPLES

It has been recently reported that a bacteriophage/virus produced by the bacteria *Pseudomonas aeruginosa* contributes to the formation and function of *Pseudomonas aeruginosa* biofilms. In particular, it has been reported that Pf bacteriophage assemble biofilms into a liquid crystal and that this crystalline organization contributes to biofilm function, including adhesiveness and antibiotic tolerance. See Secor et al., *Cell Host & Microbe.*, 18(5):549-559 (2015). In light of these data implicating Pf bacteriophages in biofilm structure and function, vaccines and monoclonal antibodies that target Pf bacteriophages have been generated to disrupt *Pseudomonas aeruginosa* biofilms.

Example 1—Role of Pf-Family Phage in Biofilm Formation

Filamentous bacteriophage are produced by *P. aeruginosa* during the biofilm mode of growth (see Rice et al., The ISME Journal (2009) 3, 271-282). A mutant not capable of producing Pf4, PA0728 (FIGS. 2A and 2B) (see Castang and Dove, J Bacteriol. September 2012; 194(18): 5101-5109), exhibited differences in morphology (FIG. 2C), adhesion (FIG. 2D), antibiotic susceptibility (FIG. 2E), and matrix organization (birefringence, FIG. 2F).

Example 2—Inhibition of Biofilms by Antiserum

Figure 4:
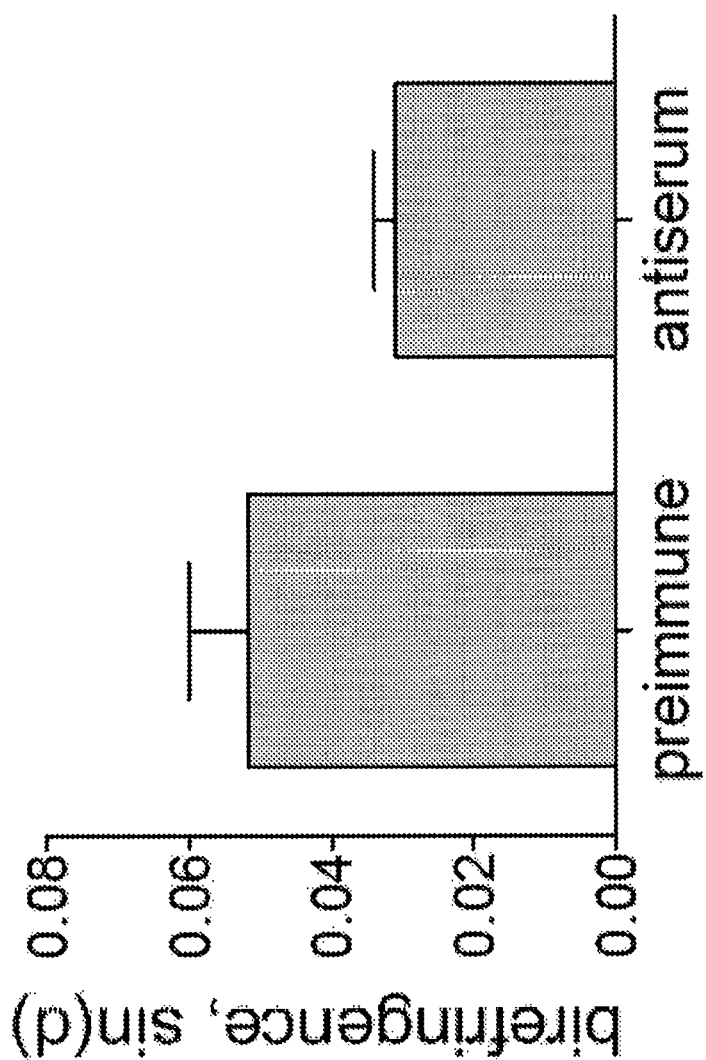
FIG. 4 shows that serum from rabbits immunized with whole Pf phage prevents biofilm formation. Biofilm formation was assayed by quantification of birefringence (liquid crystal-like organization of the biofilm matrix) of PA01 cultures 18 h after seeding and treatment with serum from rabbits before or after immunization against Pf4 phage.
Figure 5:
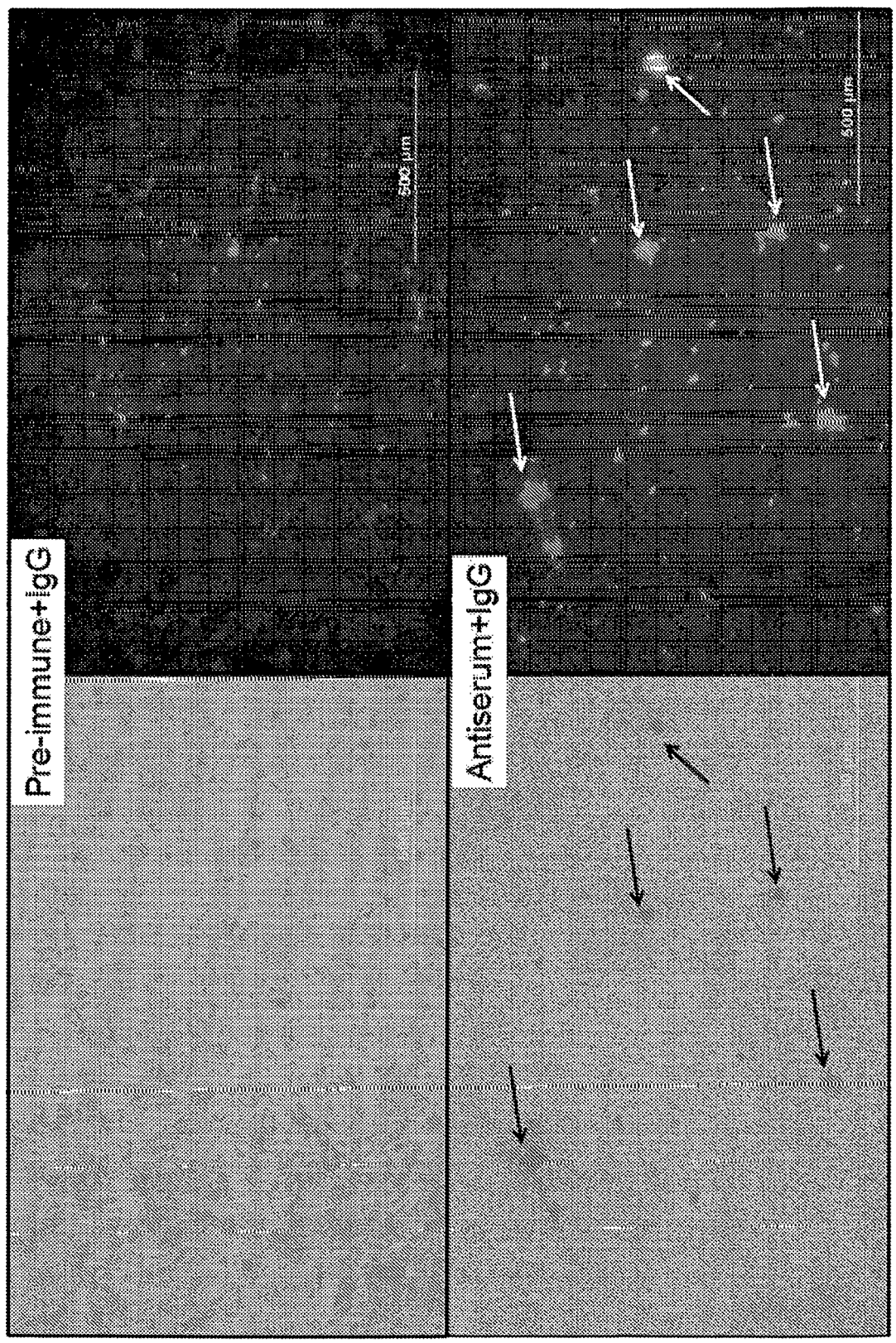
FIG. 5 shows that the addition of secondary antibodies (IgG) to biofilms pre-treated with antiserum undergo aggregation and clumping. Serum from rabbits before (pre-serum) or after immunization against Pf4 phage (anti-serum) was added to cultures of a strain of PA01. Then, a fluorescently labeled secondary antibody against rabbit IgG was used to visualize the clustering of bacteria. Confocal microscopy images are shown on the Left side of the image while fluorescence microscopy images are shown on the Right.
Figure 6:
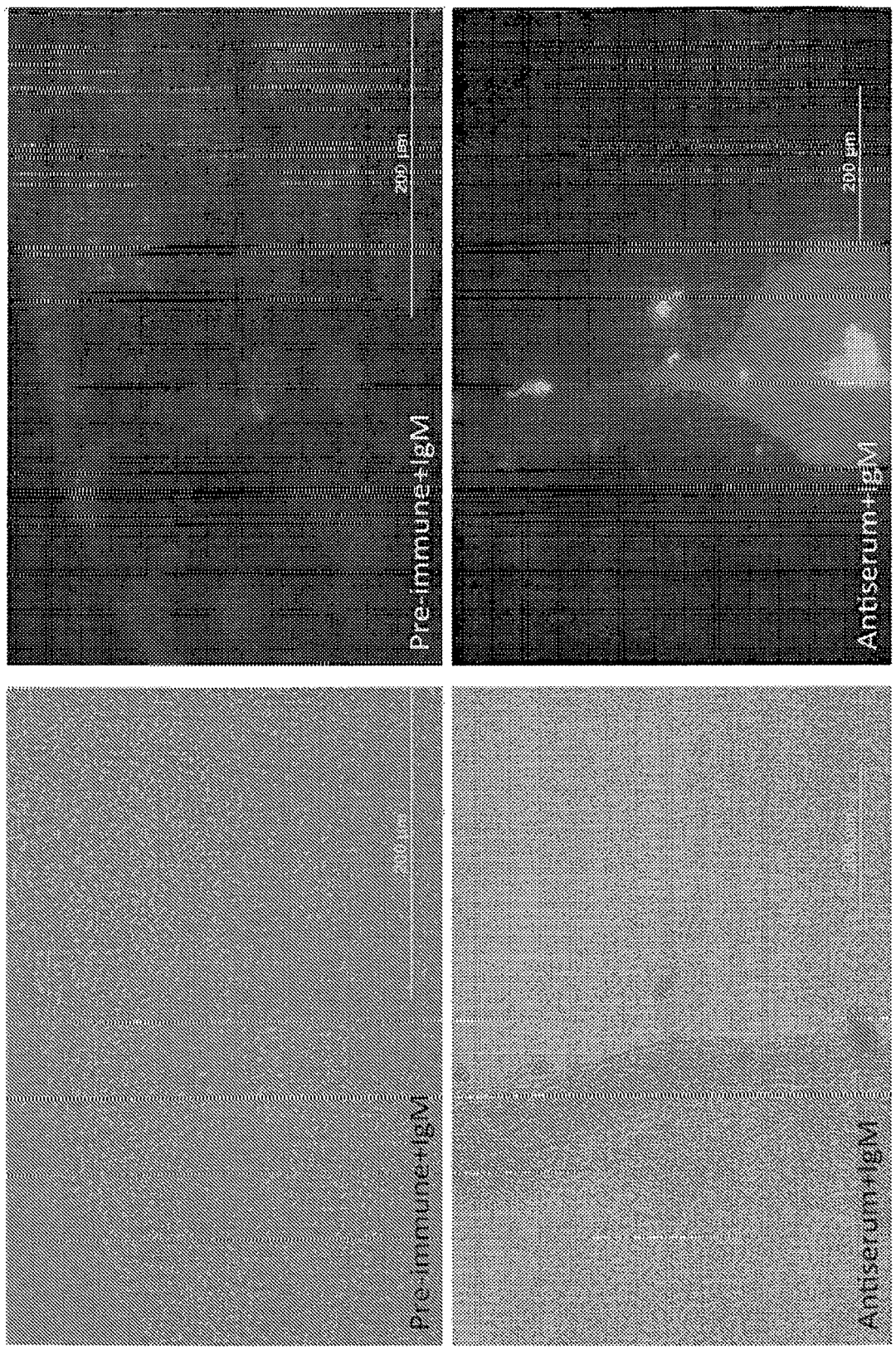
FIG. 6 shows that the addition of secondary antibodies (IgM) to biofilms pre-treated with antiserum undergo aggregation and clumping. Serum from rabbits before (pre-serum) or after immunization against Pf4 phage (anti-serum) was added to cultures of *P. aeruginosa* strain PA01. Then, a fluorescently labeled secondary antibody against rabbit IgM was used to visualize the clustering of bacteria. Confocal microscopy images are shown on the Left side of the image while fluorescence microscopy images are shown on the Right.

The method of preventing biofilm formation by creating vaccines and monoclonal antibodies that target Pf bacteriophage was evaluated. Specifically, rabbits were immunized with CoaB peptide, and the ability of their sera to neutralize biofilm formation was examined. This antiserum was found to inhibit biofilm formation, alter antibiotic tolerance (FIG. 3), and alter the overall organization of the biofilm matrix (reduced birefringence, FIG. 4), suggesting that anti-CoaB antibodies present in the serum are capable of disrupting *P. aeruginosa* biofilms producing the filamentous bacteriophage Pf4. The addition of secondary antibodies (e.g., fluorescently labeled anti-rabbit IgG and IgM) to *P. aeruginosa* biofilms pre-treated with anti-Pf4 antibodies altered the gross morphology of *P. aeruginosa* biofilms (FIGS. 5 and 6).

Example 3—Production of Monoclonal Antibody

Monoclonal antibodies that target Pf4, including three IgG and two IgM antibodies, were developed as a new class of anti-microbial for use against multi-drug resistant *P. aeruginosa*. These antibodies were generated using standard, well-established techniques, generally as described in hypertext transfer protocol://www.currentprotocols.com/WileyCDA/CPIJnit/refld-im0205.html. In brief, the CoaB peptide in question was conjugated to immunogenic proteins in order to elicit an immune response in rabbits and/or mice. Clones were then isolated from individual animals with strong serum responses to the peptide in question and these were fused to competent cells to generate hybridomas. These were then grown in culture and monoclonal antibodies were harvested from the cell culture supernatants. The specificity of these against CoaB peptide was then confirmed and five clones with the greatest specificity were selected for further development.

The variable regions of the three mouse IgG anti-Pf4 monoclonal antibodies were sequenced. The VH, VL, and CDR sequences of IgG Ab #1 (1A8), IgG Ab #2 (2D4) and IgG Ab #3 (3D6) are provided below.

IgG Ab #1 VH:
(SEQ ID NO: 2)
EVKLVESGGDLVKPGGSLKLSCAASGFTFSSYVMSWVRQTPEKRLEWVAS

ISSGGSTYYPDSVKGRFTISRDNARNILYLQMSSLRSEDTAMYYCLRGQD

YGAAYWGQGTLVTVSA.

(SEQ ID NO: 3)
GAAGTGAAGCTGGTGGAGTCTGGGGGAGACTTAGTGAAGCCTGGAGGGTC

CCTGAAACTCTCCTGTGCAGCCTCTGGATTCACTTTCAGTAGCTATGTCA

TGTCTTGGGTTCGCCAGACTCCAGAAAAGAGGCTGGAGTGGGTCGCATCC

ATTAGTAGTGGTGGTAGCACCTACTATCCAGACAGTGTGAAGGGCCGATT

CACCATCTCCAGAGATAATGCCAGGAACATCCTGTACCTGCAAATGAGTA

GTCTGAGGTCTGAGGACACGGCCATGTATTACTGTTTAAGAGGCCAGGAC

TACGGCGCCGCTTACTGGGGCCAAGGGACTCTGGTCACTGTCTCTGCA.

IgG Ab #1 VL:
(SEQ ID NO: 4)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCWQGTHFP

QTFGGGTKLEIK.

(SEQ ID NO: 5)
GATGTTGTGATGACCCAGACTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CAGACGTTCGGTGGAGGCACCAAGCTGGAAATCAAA.

IgG Ab #1 CDR:
CDR-H1
(SEQ ID NO: 6)
GFTFSSYV.

CDR-H2
(SEQ ID NO: 7)
ISSGGST.

CDR-H3
(SEQ ID NO: 8)
LRGQDYGAAY.

CDR-L1
(SEQ ID NO: 9)
QSLLDSDGKTY.

CDR-L2
(SEQ ID NO: 10)
LVS.

CDR-L3
(SEQ ID NO: 11)
WQGTHFPQT.

IgG Ab #2 VH:
(SEQ ID NO: 12)
EVQLQQSGTVLARPGASVKMSCKASGYSFTSYWMHWVKQRPGQGLEWIGA

IYPGNSDTSYNQKFKGKAKLTAVTSASTAYMELSCLTNEDSAVFYCTRSQ

FYSGSSEDAMDYWGQGTSVTVSS.

(SEQ ID NO: 13)
GAGGTTCAGCTCCAGCAGTCTGGGACTGTGCTGGCAAGGCCTGGGGCTTC

CGTGAAGATGTCCTGCAAGGCTTCTGGCTACAGCTTTACCAGCTACTGGA

TGCACTGGGTAAAACAGAGGCCTGGACAGGGTCTAGAATGGATTGGTGCT

ATTTATCCTGGAAATAGTGATACTAGTTACAACCAGAAGTTCAAGGGCAA

GGCCAAACTGACTGCAGTCACATCCGCCAGCACTGCCTACATGGAGCTCA

GCTGCCTGACAAATGAGGACTCTGCGGTCTTTTACTGTACAAGATCCCAA

TTTTACTCCGGTAGTAGCGAGGATGCTATGGACTACTGGGGTCAAGGAAC

CTCAGTCACCGTCTCCTCA.

IgG Ab #2 VL:
(SEQ ID NO: 14)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYFCFQGSHVP

WTFGGGTKLEIK.

(SEQ ID NO: 15)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTTTCAAGGTTCACATGTTCCG

TGGACGTTCGGTGGAGGCACCAAGCTGGAAATCAAA.

IgG Ab #2 CDR:
CDR-H1
(SEQ ID NO: 16)
GYSFTSYW.

CDR-H2
(SEQ ID NO: 17)
IYPGNSDT.

CDR-H3
(SEQ ID NO: 18)
TRSQFYSGSSEDAMDY.

CDR-L1
(SEQ ID NO: 19)
QSIVHSNGNTY.

CDR-L2
(SEQ ID NO: 20)
KVS.

-continued

CDR-L3
(SEQ ID NO: 21)
FQGSHVPWT.

IgG Ab #3 VH:
(SEQ ID NO: 22)
QIQLVQSGPELKKPGETVKISCKASGYTFTNYGMNWLKQAPGKGLKWMGW

INTNTGEPTYAEEFKGRFAFSLETSASTAYLQINNLKNEDTATYFCARKD

YRYWFAYWGQGTLVTVSA.

(SEQ ID NO: 23)
CAGATCCAGTTGGTGCAGTCTGGACCTGAGCTGAAGAAGCCTGGAGAGAC

AGTCAAGATCTCCTGCAAGGCTTCTGGGTATACCTTCACAAACTATGGAA

TGAACTGGCTGAAGCAGGCTCCAGGAAAGGGTTTAAAGTGGATGGGCTGG

ATAAACACCAACACTGGAGAGCCAACATATGCTGAAGAGTTCAAGGGACG

GTTTGCCTTCTCTTTGGAAACCTCTGCCAGCACTGCCTATTTGCAGATCA

ACAACCTCAAAAATGAGGACACGGCTACATATTTCTGTGCAAGAAAGGAC

TATAGGTACTGGTTTGCTTACTGGGGCCAAGGGACTCTGGTCACTGTCTC

TGCA.

IgG Ab #3 VL:
(SEQ ID NO: 24)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

FTFGSGTKLEIK.

(SEQ ID NO: 25)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCA

TTCACGTTCGGCTCGGGGACAAAGTTGGAAATAAAA.

IgG Ab #3 CDR:
CDR-H1
(SEQ ID NO: 26)
GYTFTNYG.

CDR-H2
(SEQ ID NO: 27)
INTNTGEP.

CDR-H3
(SEQ ID NO: 28)
ARKDYRYWFAY.

CDR-L1
(SEQ ID NO: 29)
QSIVHSNGNTY.

CDR-L2
(SEQ ID NO: 30)
KVS.

CDR-L3
(SEQ ID NO: 31)
FQGSHVPFT.

Example 4—Inhibition of Biofilms by Monoclonal Antibody

Figure 7:
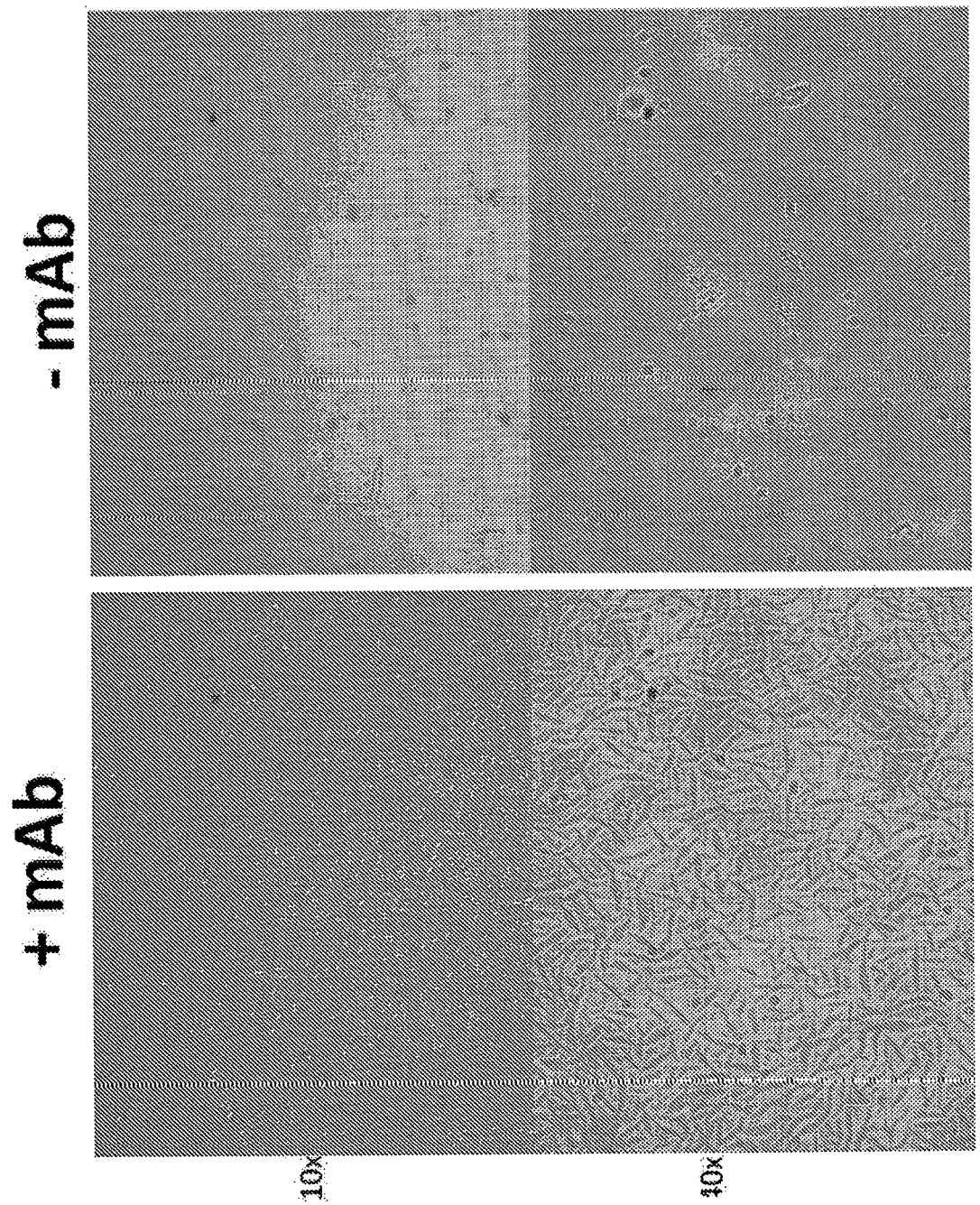
FIG. 7 shows that monoclonal antibody directed against Pf-family bacteriophage disrupt tactoidal (crystalline) structure formation by Pf4-polymer solutions. For these experiments, a panel of monoclonal antibodies were generated against the coat protein (CoaB) of Pf4 bacteriophage. All of these monoclonal antibodies had similar effects on tactoidal structures.
Figure 8:
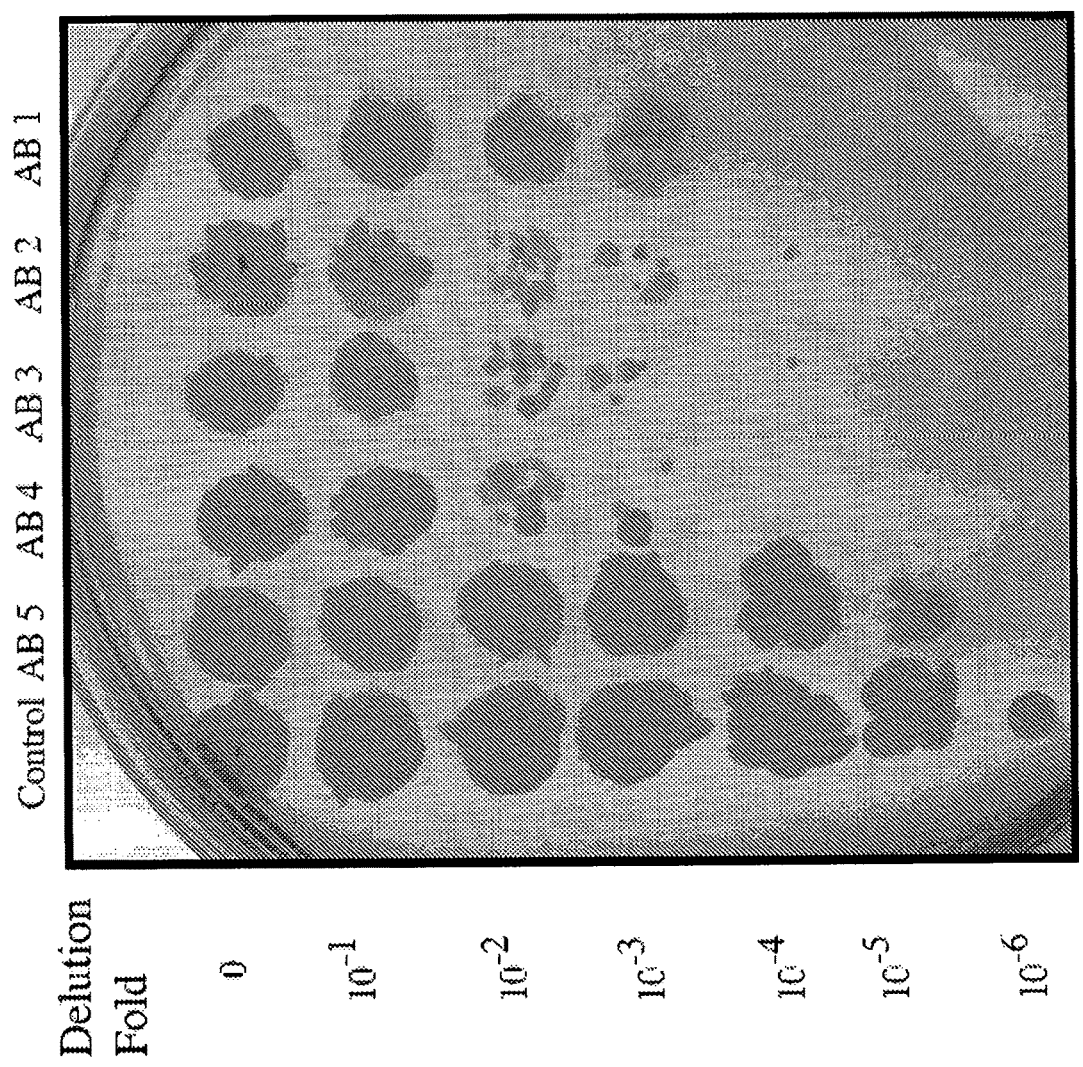
FIG. 8 shows a semi quantitative dot colony-forming assay that demonstrates that the anti-Pf4 monoclonal antibodies facilitate the penetration of antibiotics into biofilms (exposed to 10 µg/ml of Tobramycin). These experiments were performed by adding one of 4 monoclonal antibodies (AB1, AB2, AB3, AB4) that recognize Pf phage or a control antibody that does not recognize pf phage (AB5) to dilutions of biofilm cultures of the PA01 strain of *P. aeruginosa*. The size of the bacterial colonies that grow in this setting is inversely related to the penetration of antibiotic through the biofilm.
Figure 10:
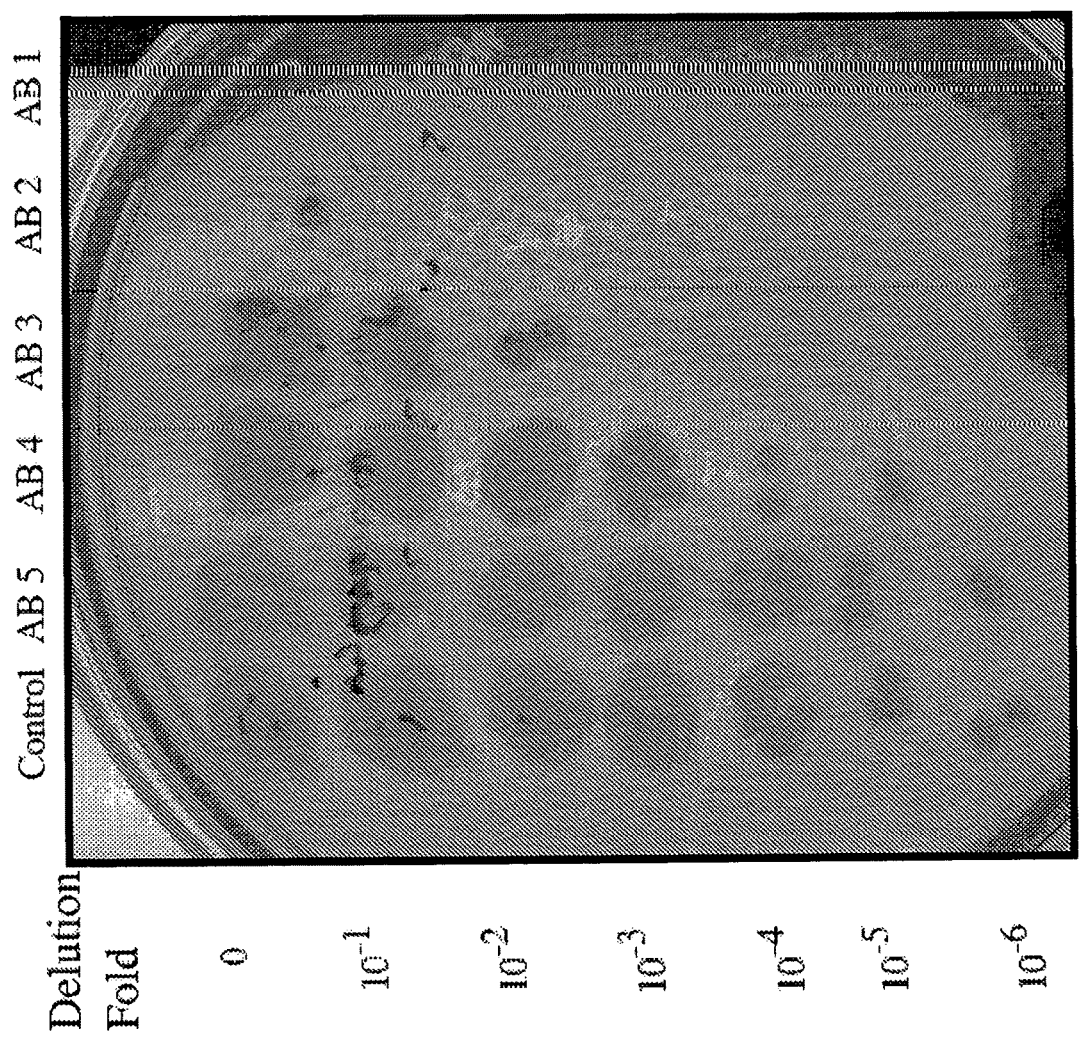
FIG. 10 shows a semi quantitative dot colony-forming assay that demonstrates that the anti-Pf4 antibodies facilitate the penetration of antibiotics into biofilms (exposed to 50 µg/ml of Tobramycin). These experiments were performed by adding one of 4 monoclonal antibodies (AB1, AB2, AB3, AB4) that recognize Pf phage or a control antibody that does not recognize pf phage (AB5) to dilutions of biofilm cultures of the PA01 strain of *P. aeruginosa*. The size of the bacterial colonies that grow in this setting is inversely related to the penetration of antibiotic through the biofilm. Compared to FIG. 8, these data show that the effect of the antibodies was more intense when the biofilms were exposed to higher concentration of Tobramycin (50 ug/ml compared to 10 ug/ml). In that case AB1 and AB2 cause to 7 orders of magnitude reduction in *P. aeruginosa*. concentration that survived the Tobramycin treatment compare to the control.
Figure 12:
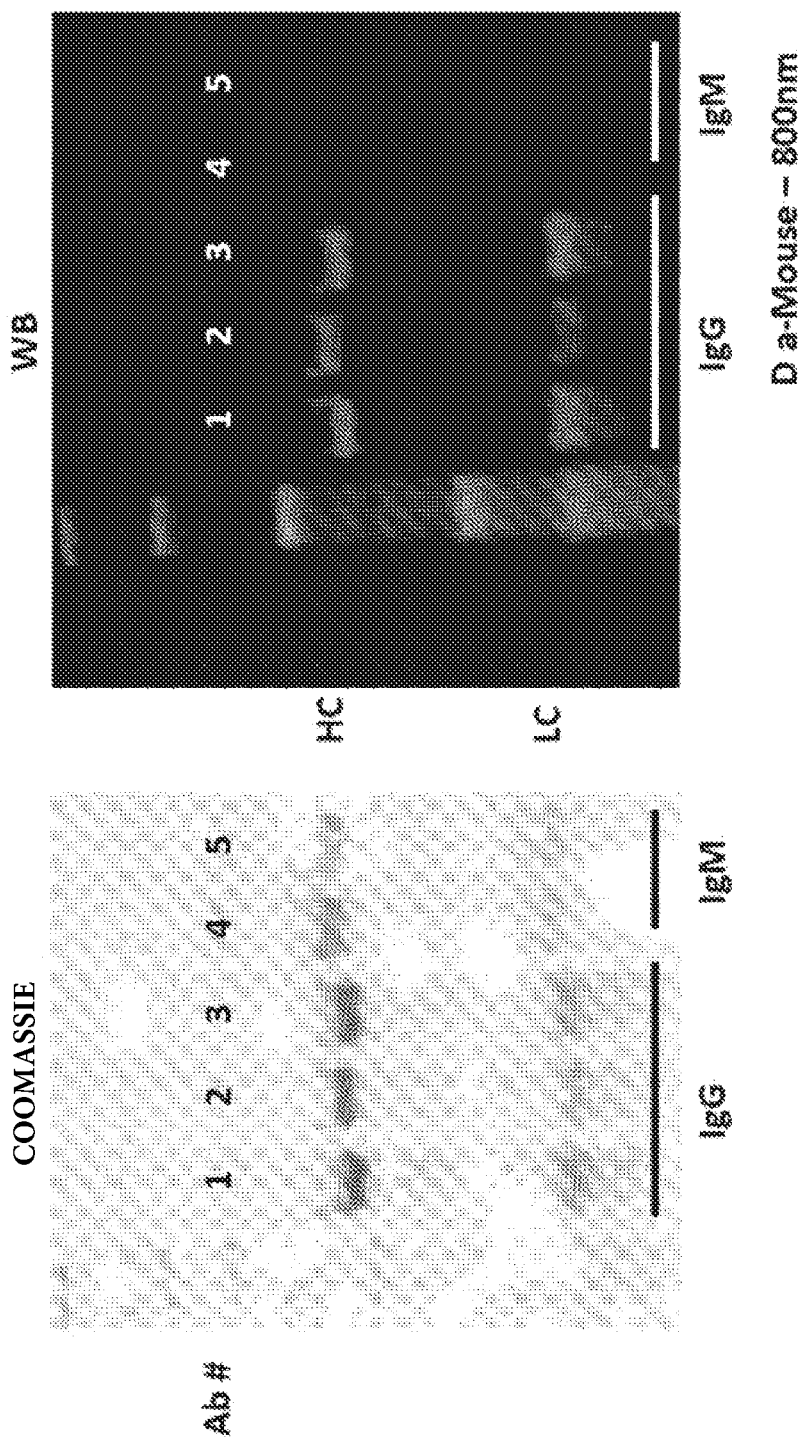
FIG. 12 shows detection of the heavy and light chains of 5 different monoclonal antibodies by COOMASSIE staining and by Western Blot (WB). Three of the antibodies are IgG and two of the antibodies are IgM. All of these antibodies were generated against the Pf phage coat protein sequence GVIDTSAVESAITDGQGDM (SEQ ID NO: 1).
Figure 13:
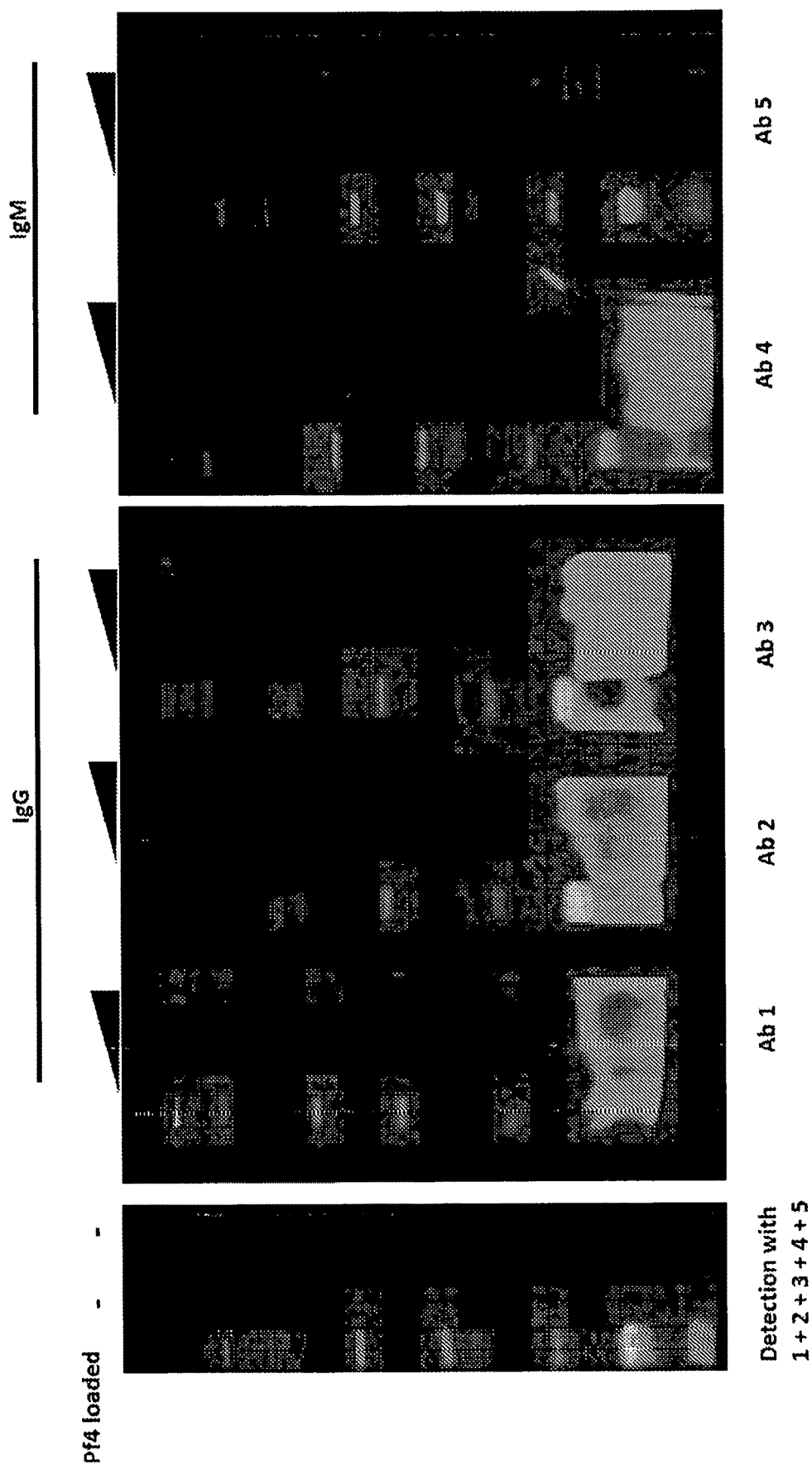
FIG. 13 shows detection of the CoaB coat protein of Pf bacteriophage by 5 different monoclonal antibodies by Western Blot (WB). Three of the antibodies are IgG and two of the antibodies are IgM. One of the IgM (Ab5) does not recognize Pf4 phage and is included here as a control.

Also tested is whether the monoclonal antibodies produced according to Example 2 can serve as effective antibiotic drugs that could be used in conjunction with conventional antibiotics, as current therapeutic options for treatment of multidrug-resistant *P. aeruginosa* are very limited. As shown in FIG. 7, the mAbs prevented liquid crystal formation of Pf4-polymer solutions suggesting that the mAbs have the same activities as the anti-Pf4 antibodies present in the antiserum of Example 2.

As used herein, the singular terms "a," "an," and "the" include plural referents unless the context clearly dictates otherwise. Thus, for example, reference to a marker can include multiple markers unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. An immunogenic composition comprising a pharmaceutically acceptable carrier and an immunogenic peptide of CoaB protein of Pf4-family bacteriophage, wherein the peptide consists of the amino acid sequence of SEQ ID NO: 1 and is conjugated to an immunogenic protein.

2. A method of eliciting an immune response against Pf4-family bacteriophage in an animal or a human subject comprising administering to said animal or said human subject the immunogenic composition of claim 1.

* * * * *